(12) United States Patent
Frank

(10) Patent No.: US 11,741,689 B2
(45) Date of Patent: Aug. 29, 2023

(54) AUTOMATED, DYNAMIC DIGITAL FINANCIAL MANAGEMENT METHOD AND SYSTEM WITH PHSYICAL CURRENCY CAPABILITIES

(71) Applicant: David Godwin Frank, Redondo Beach, CA (US)

(72) Inventor: David Godwin Frank, Redondo Beach, CA (US)

( * ) Notice: Subject to any disclaimer, the term of this patent is extended or adjusted under 35 U.S.C. 154(b) by 0 days.

(21) Appl. No.: 17/140,942

(22) Filed: Jan. 4, 2021

(65) Prior Publication Data

US 2022/0121873 A1    Apr. 21, 2022

Related U.S. Application Data

(63) Continuation-in-part of application No. 17/075,442, filed on Oct. 20, 2020.

(51) Int. Cl.
*G06V 10/75* (2022.01)
*G06V 20/10* (2022.01)
(Continued)

(52) U.S. Cl.
CPC ............ *G06V 10/751* (2022.01); *G06V 20/10* (2022.01); *G06V 30/41* (2022.01);
(Continued)

(58) Field of Classification Search
CPC .................................................. G06V 10/751
See application file for complete search history.

(56) References Cited

U.S. PATENT DOCUMENTS 7,895,096 B1    2/2011  Vu
7,895,102 B1    2/2011  Wilks
(Continued)

FOREIGN PATENT DOCUMENTS

CN        106056371 A     10/2016
WO    WO-2006116029 A2 *  11/2006  ............... G06K 9/38

OTHER PUBLICATIONS

Forwood, S.E., Ahern, A.L. Marteau, T.M. et al., Offering with—category food swaps to reduce energy density of food purchases; a study using an experimental online supermarket. Int J Behav Nutr Phys Act 12, 85 (2015). https://doi.org/10.1186/s12966-015-0241-1(Year 2015).

(Continued)

*Primary Examiner* — Scott C Anderson
(74) *Attorney, Agent, or Firm* — Haverstock & Owens, A Law Corporation

(57) ABSTRACT

An automated, dynamic digital financial management tool is described herein. The financial management tool enables a user to access all forms of payments, debt and transactions to be deducted automatically depending on which form of payment is chosen. The financial management tool documents every item/service purchased. The documentation enables a company/manufacturer/store to provide marketing and recall information to the user. The financial management tool is able to include any and/or all financial aspects of a user's life. The financial management tool is able to be implemented using a universal card. The financial management tool is able to include a pay station to receive payments. The financial management tool is able to include automated services. An automated, dynamic health management system is also described herein.

21 Claims, 5 Drawing Sheets

(51) Int. Cl.
*G06V 30/41* (2022.01)
*G06Q 30/0601* (2023.01)
*G16H 10/60* (2018.01)
*G06Q 30/0226* (2023.01)
*G06Q 30/0201* (2023.01)
*G06Q 40/02* (2023.01)

(52) U.S. Cl.
CPC ..... *G06Q 30/0201* (2013.01); *G06Q 30/0229* (2013.01); *G06Q 30/0631* (2013.01); *G06Q 40/02* (2013.01); *G16H 10/60* (2018.01)

(56) References Cited

U.S. PATENT DOCUMENTS

| | | | |
|---|---|---|---|
| 7,898,096 | B1 | 3/2011 | Krupenkin |
| 8,944,234 | B1 * | 2/2015 | Csulits ................ G07D 7/12 382/140 |
| 9,495,703 | B1 | 11/2016 | Kaye, III |
| 10,248,964 | B1 | 4/2019 | Neeman |
| 11,113,709 | B2 | 9/2021 | Nelsen |
| 11,205,212 | B1 | 12/2021 | Iacono et al. |
| 2005/0046584 | A1 | 3/2005 | Breed |
| 2008/0195870 | A1 | 8/2008 | Posamentier |
| 2008/0298649 | A1 * | 12/2008 | Ennis ................ G06V 40/45 382/125 |
| 2009/0006196 | A1 | 1/2009 | Barkan et al. |
| 2009/0024540 | A1 | 1/2009 | Ryder |
| 2009/0048957 | A1 | 2/2009 | Celano |
| 2010/0165093 | A1 | 7/2010 | Sugio |
| 2010/0168585 | A1 | 7/2010 | Fujii |
| 2012/0271705 | A1 | 10/2012 | Postrel |
| 2013/0103484 | A1 | 4/2013 | McLaughlin |
| 2013/0159084 | A1 | 6/2013 | Smith |
| 2013/0339124 | A1 | 12/2013 | Postrel |
| 2014/0067597 | A1 | 3/2014 | Kirby |
| 2014/0107493 | A1 | 4/2014 | Yuen |
| 2014/0207669 | A1 | 7/2014 | Rosenberg |
| 2016/0071140 | A1 | 3/2016 | Sherman |
| 2016/0162882 | A1 | 6/2016 | McClung, III |
| 2016/0171570 | A1 | 6/2016 | Dogin |
| 2016/0189158 | A1 | 6/2016 | Eramian |
| 2017/0091801 | A1 | 3/2017 | Rothberg |
| 2017/0091851 | A1 | 3/2017 | Snow |
| 2017/0193504 | A1 | 7/2017 | Godsey |
| 2018/0095467 | A1 | 4/2018 | Perrone |
| 2018/0204280 | A1 | 7/2018 | Painter |
| 2018/0232817 | A1 | 8/2018 | Isaacson |
| 2019/0050618 | A1 * | 2/2019 | Khuri-Yakub ..... A61B 5/14552 |
| 2019/0073714 | A1 | 3/2019 | Fidanza |
| 2019/0147478 | A1 | 5/2019 | Umemura |
| 2019/0164165 | A1 | 5/2019 | Ithabathula |
| 2019/0180873 | A1 | 6/2019 | Kartoun et al. |
| 2019/0228441 | A1 | 7/2019 | Rutkin |
| 2019/0228856 | A1 | 7/2019 | Leifer |
| 2020/0184055 | A1 | 6/2020 | Storm |
| 2020/0202989 | A1 | 6/2020 | Dror |
| 2020/0297270 | A1 | 9/2020 | Ando et al. |
| 2020/0342428 | A1 * | 10/2020 | Benkreira ............. G07D 11/30 |
| 2020/0387887 | A1 | 12/2020 | Rathod |
| 2021/0035069 | A1 | 2/2021 | Parikh |
| 2022/0129936 | A1 | 4/2022 | Jung |

OTHER PUBLICATIONS

Shakespeare, King John [IV,2] line 1819, downloaded from https://www.opensourceshakespeare.org/search/search-results.php on Nov. 3, 2022(Year:1623).

Medina, Paolina, Vrinda Mittal, and Michigan Pagel. "Bumped: The Effects of Stock Ownership on Individual Spending." (2020). (Year:2020).

* cited by examiner

AUTOMATED, DYNAMIC DIGITAL FINANCIAL MANAGEMENT METHOD AND SYSTEM WITH PHSYICAL CURRENCY CAPABILITIES

CROSS-REFERENCE TO RELATED APPLICATION(S)

This application is a continuation-in-part application of co-pending U.S. patent application Ser. No. 17/075,442, filed on Oct. 20, 2020, and titled "AUTOMATED, DYNAMIC DIGITAL FINANCIAL MANAGEMENT METHOD AND SYSTEM," which are hereby incorporated by reference in their entireties for all purposes.

FIELD OF THE INVENTION

The present invention relates to health management. More specifically, the present invention relates to health management using a single device.

BACKGROUND OF THE INVENTION

Many people have multiple credit cards and/or debit cards for purchasing goods. These credit/debit cards have varying rewards and other benefits. Therefore, it is upon the user of the credit/debit cards to determine which card to use at which store. Additionally, having multiple credit/debit cards increases the chances of losing/misplacing one of the cards. Furthermore, many people are highly disorganized when it comes to their finances, particularly, when their expenses are distributed among multiple credit/debit cards and various bank/online accounts.

Many people use various applications ("apps") and simply read food labels to monitor their nutritional information. However, the manual approach even with the assistance of apps is challenging, requires a significant amount of work, and usually only lasts for a short amount of time as the user tires of all of the effort. Moreover, manually tracking the information may not be accurate as it depends on the user's efforts.

SUMMARY OF THE INVENTION

An automated, dynamic digital financial management tool is described herein. The financial management tool enables a user to access all forms of payments, debt and transactions to be deducted automatically depending on which form of payment is chosen. The financial management tool documents every item/service purchased. The documentation enables a company/manufacturer/store to provide marketing and recall information to the user. The financial management tool is able to include any and/or all financial aspects of a user's life. The financial management tool is able to be implemented using a universal card. The financial management tool is able to include a pay station to receive payments. The financial management tool is able to include automated services.

An automated, dynamic digital health management tool is described herein. The health management tool enables a user to access all forms of health/nutritional information to be analyzed automatically. The health management tool documents food items purchased. The health management tool is able to include any and/or all health aspects of a user's life. The health management tool is able to be implemented using a universal card. The health management tool is able to include automated services.

DETAILED DESCRIPTION OF THE PREFERRED EMBODIMENT

Figure 1:
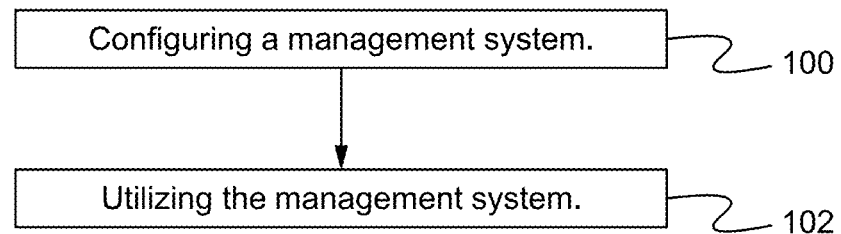
FIG. 1 illustrates a flowchart of a method of implementing a management system according to some embodiments.

An automated, dynamic digital financial management tool is described herein. The financial management tool enables a user to preload all forms of payments, debt and transactions to be deducted automatically depending on which form of payment is chosen. The financial management tool records/documents every item/service purchased. The documentation of the purchases includes recording the SKU code, the company/store, where the item/service was purchased, and/or other information. The documentation enables a company/manufacturer/store to provide marketing (e.g., coupons) and recall information to the user. The financial management tool is able to include any and/or all financial aspects of a user's life. The aspects are able to be classified such as lines of credit/payment, expenses, income, and so on. The financial management tool is able to be implemented using a universal card.

The universal card is able to store information for any number of lines of credit or other sources of funds. For example, a user has 3 credit cards and a debit card, and when a user uses the universal card, the universal card automatically determines the appropriate line of credit to use. Furthering the example, the 3 credit cards include a Target® credit card, a Visa® credit card, and a Discover® credit card, and when purchasing items at Target®, the Target® credit card information is automatically selected for payment since it provides the user a 5% discount on all items, but when at a gas station, the Visa® credit card provides double points, so that credit card information is automatically selected for payment. The method of automatic selections is able to be implemented in any manner such as user-specified and then automatically, computer-determined, or a combination thereof. For example, the universal card first determines which line of credit is usable at this location (e.g., if Store X does not accept Discover® cards, then that is removed from the options list). Furthering the example, a user is able to specify that they prefer cash discounts over credit card points, so the universal card is able to prioritize cash discounts over points. The universal card is able to intelligently compare 3× points versus 2× points versus 1× points, and select the line of credit which provides the highest amount/number of points. The universal card is able to store and/or access a set of rules or other algorithm which determines which payment source is utilized.

The universal card is able to compare the purchase price of the items/services with the amount of credit available, and if the purchase price exceeds the amount of credit available, then the universal card would not use that line of credit or is able to divide the purchase over multiple lines of credit.

Any combination of priorities, preferences, analysis, learning, selections, implementations and/or other factors are able to be analyzed, input, determined, stored and/or used.

In some embodiments, the universal card includes a processor, memory and programming to perform the analysis and make a decision, and in some embodiments, the universal card sends information to a system (e.g., server device, mobile device) to perform the analysis and make a decision.

In some embodiments, the universal card is usable similar to credit cards with a magnetic strip to be swiped, a microchip to be inserted into a microchip reader, and/or the microchip to be detected/read based on a tap by a microchip reader. In some embodiments, a digital version of the universal card is stored on a mobile device (e.g., smart phone, smart watch), so that the user does not need to carry a physical card. In some embodiments, the universal card is used in conjunction with Apple Pay, Google Pay, and/or similar digital payment systems.

In some embodiments, a physical pay station is implemented to utilize the universal card and/or another user recognition system. For example, the pay station includes a retina scanner, a fingerprint scanner and/or other biometric scanner to determine who the user is, and then trigger the automatic payment based on the lines of credit associated with the particular user. In some embodiments, the pay station includes a pulse detection implementation to provide against specific types of fingerprint theft or other theft.

As mentioned, the management tool is able to include many sources for payment such as credit cards, debit cards, house lines of credit, business lines of credit, checking accounts, savings accounts, digital payment accounts (e.g., PayPal), digital business accounts (e.g., Amazon/Synchrony bank), bitcoin accounts, gift cards, stock trading accounts, retirement accounts, social security accounts, government assistance accounts, and/or any other financial sources.

In some embodiments, the management tool is configured to communicate among the many payment sources to exchange payments that otherwise would not be exchangeable. For example, if a user has a Starbucks® gift card, the user is able to input that gift card into the management tool, and the management tool is able to perform a background transaction where the gift card is usable at a non-Starbucks location. Behind the scenes, the financial organizations are able to perform the transactions such that each location is made whole. In an example, using a peer-to-peer system, when another user purchases an item from Starbucks®, the gift card of the current user is applied to that purchase, and the monetary transaction from the other user is transferred in a manner that the current user is able to purchase from the non-Starbucks location.

The management tool is able to record and store many sources of expenses/debts such as by tracking all of the purchases a user makes at physical locations and digital locations. The details of the purchases are able to be as specific or as general as desired or needed. For example, a supermarket purchase is able to include which items were purchased, the date of the purchase, the expiration dates of the items purchased, how frequently the items are purchased (e.g., based on historical purchase information), trends of purchases, how the items were purchased, the location of the purchase, and so on. Other expenses/debts are able to be recorded by the management tool such as a house mortgage, car loan, business loan, other loans, child support, spousal support, utilities, activities, health insurance, and other debts.

The management tool is able to record and store many sources of income such as occupational income, rental income, stock/bond income, and others.

Based on all of the financial information available to the management tool, the management tool is able to assist a user in paying for items, purchasing items, determining which items to purchase or not, and providing additional information. For example, a user's debt-to-income ratio is able to be calculated and used to assist in making purchases such as purchasing a house, and guiding the user to a house that is within the user's budget.

The management tool is able to be used to prevent financial crime. For example, if an anomalous purchase is detected, additional verification is able to be requested, an alert is able to be triggered, and/or the purchase is able to be blocked. For example, if a purchase is detected in a country where the user is not located, then an alert is able to be sent to the user's phone, where the user is required to input a code to verify that he is the user attempting to make the purchase.

Based on the financial information of a user, targeted marketing is able to be implemented. Not only is the marketing based on a user's purchases, which will be known using the management tool, but the marketing is able to be based on the user's current financial situation, which enables more effective targeting. For example, a user with a low debt-to-income ratio is able to be marketed more expensive items, whereas a user with a high debt-to-income ratio is marketed less expensive items.

The management tool is able to be used for tax planning purposes to be documented into a Schedule C on a 1040 form. For example, if the management tool is used for a business, and the user (business owner) purchases items for the business, the purchase is an expense for that business. At the end of the year, the management tool is able to provide a detailed accounting of the income and expenses throughout the year.

The management tool is able to perform currency exchanges. For example, if the user travels to another country, the management tool is able to pay in the currency of the current country, regardless of the user's country of origin.

The management tool is able to be used to as a money exchange (e.g., person to person, person to business, or business to business).

All of the information is gathered automatically by the management tool such that the user does not need to manually enter information. The management tool is able to perform all of the transactions described herein in real-time.

In some embodiments, a user subscribes to gain access to the management tool.

A management company providing the management tool is able to receive a subscription payment (e.g., monthly, yearly, one-time). The management company is also able to receive a percentage of a purchase (e.g., 3% of the purchase price goes to the management company). The management company is also able to receive referral fees or marketing fees based on the directed marketing to the subscribers.

In some embodiments, the management tool analyzes and detects patterns of purchases by a user, and automatically suggests or makes purchases based on the detected patterns. For example, the management tool determines after a month of analysis, that a user purchases a gallon of milk every Sunday from Store X, so the management tool provides offers to have milk delivered once a week, or enables milk to be available in a pre-paid pickup from Store X every Sunday.

FIG. 1 illustrates a flowchart of a method of implementing a management system according to some embodiments. In the step 100, the management system is configured for a user. Configuring the management system is able to be performed manually, automatically or semi-automatically. Configuring is able to include a user subscribing to the management system. Subscribing is able to be performed similarly to other subscriptions such as inputting personal information and/or retrieving personal information (e.g., from a social networking site). After subscribing, the user's financial information is acquired. The user is able to manually input information such as credit card information, bank account information, and/or any other financial information. In a semi-automatic implementation, the user is able to manually enter some financial information, and the system (e.g., server) is able to acquire additional financial information of the user. In another example, the user provides his social security number, and the system retrieves banking information associated with the user, but the user inputs gift card information and other information not found by the automated search. In an automatic implementation, the system automatically retrieves the user's financial information. For example, based on facial recognition (or other biometric recognition), the system determines who the user is, and then accesses financial information for that user by communicating with banks, credit card companies, and other financial companies.

Configuring the management system is able to include providing personal preferences and/or automatically determining which line of credit is used to pay for which goods/services. For example, a user is able to specify which line of credit is utilized by the management system when purchasing items at which location. Similarly, the management system is able to automatically determine which line of credit is utilized at which location. Since the management system is able to include many sources of credit/payment, the management system is able to prioritize the sources of credit/payment. For example, if the management system is managing gift cards for the user, those gift cards may be used up first since they may have an expiration date. In another example, lines of credit which provide the highest discount or rewards are utilized. An exemplary priority list includes:
1. Gift cards
2. Lines of credit with a purchase discount
3. Lines of credit with a monetary reward
4. Lines of credit with the highest point reward
5. Checking account (default)

In another example, a table or other data structure is utilized to determine which credit/payment source is used for which purchase/store. An exemplary table is shown:

| Store | Credit/Payment Source |
|---|---|
| Target | Target card |
| Macy's | Visa card |
| Old Navy | Visa card |
| Lucky | Mastercard card |

By matching up the store with the credit/payment source preemptively, the process of determining the appropriate card to use is more efficient, and a determination is not necessary while a purchase is being made. In some embodiments, to further optimize the process, after determining the credit/payment sources for a user, the stores within a specified area (e.g., 20 mile radius) are analyzed and added to the data structure with the corresponding selected credit/payment source. In some embodiments, using GPS or other geolocation implementation, the system is able to detect that a user is near a certain location (e.g., business), and is able to preemptively determine the most beneficial credit/payment source for that location. For example, if the user travels and based on GPS, it is determined that the user is visiting Store X, the system is able to perform the analysis to determine the credit card with the best perks for Store X, and saves the information in the data structure, so that when the user purchases items, the appropriate credit/payment source is already determined.

In the step 102, the management system is utilized. Utilizing the management system is able to include many different features such as making a payment, automatically making additional purchases, providing targeted marketing, and any other features discussed herein. As mentioned in terms of configuring the management system, when a user makes a purchase, the management system determines where the payment is coming from. Based on preferences/priorities, the most financially beneficial source of credit/payment is selected. For example, when a user goes to a store and uses that store's line of credit, they may be given a discount on the purchase, so it would be most beneficial to use that store line of credit. The management system is able to include sets of rules (e.g., in a database/table format) which determine which line of credit to use. The rules/criteria are able to be organized and implemented in any manner such as specific and general rules. For example, the rules are able to specify: use line of credit A for Stores X, Y, Z and line of credit B for Stores J, K, L. In another example, the rules are able to specify: use line of credit A for stores in the grocery category, and line of credit B for gas stations and sporting goods stores. If a purchase does not fall in a category, a default line of credit/payment is able to be used. In some embodiments, the system uses a learning algorithm to determine which line of credit to use for each store. The rules/criteria are able to be stored/implemented on a server device, a user device (e.g., smart phone), in a universal card, another device, and/or a combination thereof.

Since the management system monitors/tracks the purchases by the user, the management system is able to determine patterns of purchases and make projections for future purchases, and make those future purchases at the appropriate times. In some embodiments, the automated purchasing is able to be utilized with an automated store and an automated delivery service to have the purchased items delivered to a user.

The management system is also able to enable/perform targeted advertising based on the user's purchases and other monitored information. As described, targeted advertising is able to include monitoring and analyzing the user's purchases, as well as monitoring and analyzing other financial information of the user. For example, the system monitors and tracks all of the individual items purchased by the user including any additional helpful information such as when purchased, how often purchased, purchased at which store, coupon used, are there any complementary items purchased/to be purchased (e.g., hamburger patties and buns), SKU number, expiration date, and/or any other information. The system is also able to monitor and analyze the user's income, other family member income, expenses, bank account information and other financial information which may be used to provide an advertisement that specifically targets the user. The targeted advertisement is able to be appropriately timed (e.g., when the previously purchased product is about to expire), based on the financial status of the user, to provide a complement to a previously purchased item, based on a special event (e.g., birthday, anniversary, child's birth) and/or any other relevant information. The targeted advertising is able to be based on any characteristic of the user such as sex/gender, age, marital/relationship status, and/or any other characteristics. The targeted advertising is able to be presented to the user in any manner such as a mobile device (or any device) associated with the subscription (e.g., via corresponding login information or social networking information).

The management tool is able to be used to digitalize and store all transactions on receipts of a consumer/user. Any aspect of a transaction of a user, consumer, business, and/or other entity is able to be stored using the management tool. Aspects of the transaction include the goods/services purchased, the time/date of the purchase, the costs involved (e.g., price paid by consumer, and retail cost, wholesale cost, profit for business).

The management tool enables users to sell/buy products/services, including making recommendations of products/services to buy/sell. The user-to-user transactions are able to be stored for the buyer and seller. The recommendations are able to be based on previously purchased items. For example, if a consumer purchases an item that uses replaceable items (e.g., a coffee maker), then recommendations/advertisements or other targeted messaging is able to be provided to the consumer by the management tool (or another service which accesses data acquired by the management tool). The recommendations are able to be based on any information/characteristics (e.g., age/gender) similar to the targeted advertising. In some embodiments, the management tool implements a social networking aspect to connect users with items that are recommended to sell and to purchase. For example, if User A has an item that he would like to sell or has been recommended to sell by the management tool, and User B would like to purchase that item or has been recommended to purchase that item, then the management tool is able to connect User A and User B. In some embodiments, the management tool connects the users regardless of their previous relationship (e.g., possibly not related), and in some embodiments, the management tool only connects the users if they have a pre-existing relationship (e.g., are in each other's social network, have friended each other).

In some embodiments, fewer or additional steps are implemented. In some embodiments, the order of the steps is modified.

Figure 2:
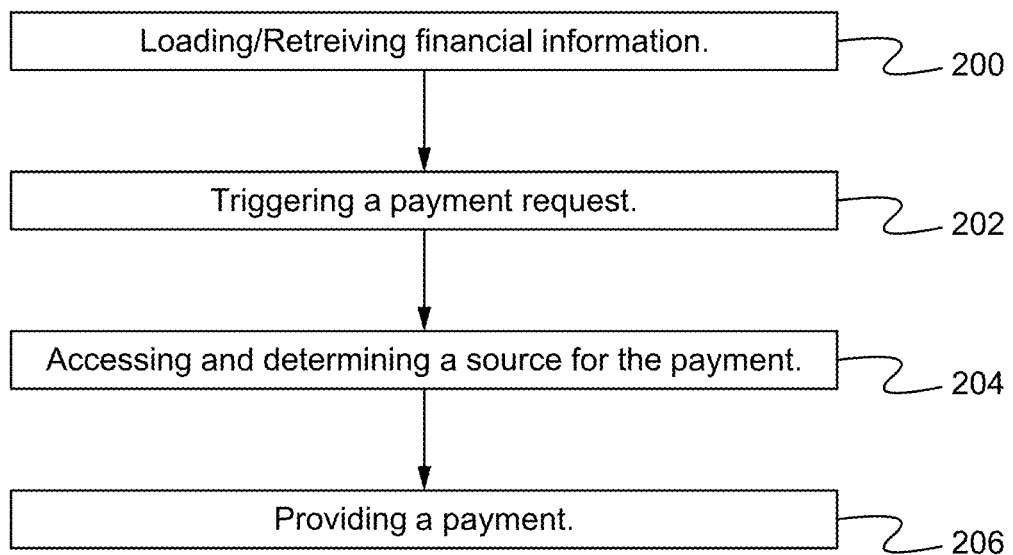
FIG. 2 illustrates a flowchart of a method of utilizing a management system for payment according to some embodiments.

FIG. 2 illustrates a flowchart of a method of utilizing a management system for payment according to some embodiments. In the step 200, financial information is loaded/retrieved. As described herein, the financial information is able to be retrieved in any manner such as being manually input by a user, and/or retrieved automatically using the management system from financial institutions. In some embodiments, retrieving the financial information includes many types of financial information as described herein such as income, credit, expenses, gift cards and more. The financial information is retrieved by and stored on a device such as a universal card, a user device (e.g., smart phone) and/or a server.

In the step 202, a payment request is triggered. The payment request is able to be triggered in any manner such as at a grocery store, where a user is requested to pay for his groceries. The payment request is able to be triggered by a standard payment processing device (e.g., a credit card reader), an online payment app, a pay station, and/or any other device. For example, the payment request includes: pay $53.25 to Store X. Additional information is able to be included in the payment request such as specific items, the date, the address of the store, and/or other information, in some embodiments. After a payment request is triggered by a payment processing device (or other device), the payment request to payment source is able to be triggered by a device such as a universal card, a user device (e.g., smart phone) and/or a server.

In the step 204, a source for the payment is determined and accessed. Upon receiving the payment request which is able to include specific information such as the location of the request, the management system determines which source for the payment to be used. As described herein, the management system is able to include a database or data structure for determining which payment source to be used for each purchase location. Determining and accessing the payment source is able to be from a device such as a universal card, a user device (e.g., smart phone) and/or a server.

In the step 206, the payment is made using the determined payment source. For example, the selected credit card information is utilized to pay the store, and the transaction is completed. The payment occurs by accessing (via a device) the payment source and receiving payment information from that source. In some embodiments, the order of the steps is modified. In some embodiments, fewer or additional steps are implemented.

Figure 3:
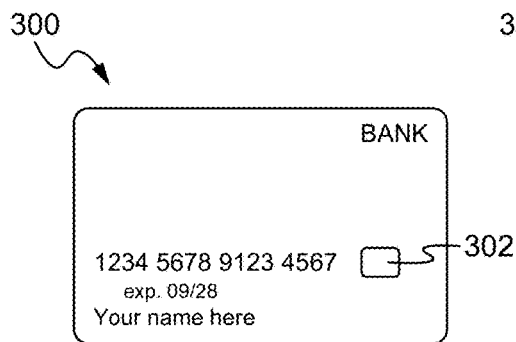
FIG. 3 illustrates a front view of a universal card according to some embodiments.

FIG. 3 illustrates a front view of a universal card according to some embodiments. The universal card 300 is able to be shaped similar to a credit card so that it is usable in standard credit card readers. The universal card 300 is able to include a microchip 302 which is able to be programmed to perform the management system tasks and/or communicate with a server device or another device to perform the management system tasks.

Figure 4:
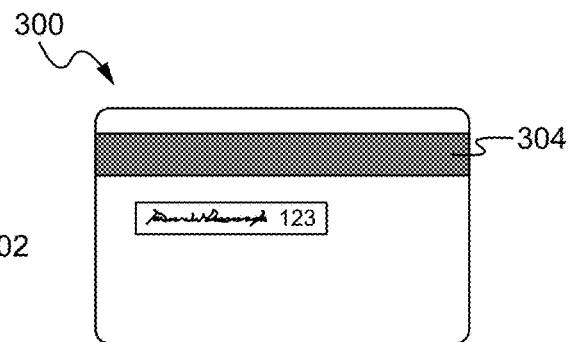
FIG. 4 illustrates a back view of a universal card according to some embodiments.

FIG. 4 illustrates a back view of a universal card according to some embodiments. The universal card 300 is also able to have a magnetic strip 304 similar to credit cards. The magnetic strip 304 is able to be swiped, and then based on the swipe, a server device or another device is able to be triggered that a payment is to be made. The server device or other device then determines from which payment source the payment should come from, and generates the payment information.

Figure 5:
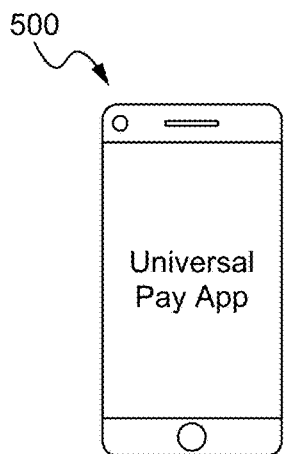
FIG. 5 illustrates a mobile device according to some embodiments.

FIG. 5 illustrates a mobile device according to some embodiments. The mobile device 500 is able to be any mobile device such as a smart phone, a smart watch, and an autonomous vehicle. The mobile device 500 is able to be configured to implement the management system described herein. When a payment request is received, the management system on the mobile device 500 is able to perform the steps of providing a payment from a payment source based on the criteria/rules of the management system. The mobile device 500 is able to be used similar to Apple Pay or Google Pay in terms of receiving a payment request from a store's pay station which accepts digital payment. Unlike the previous payment systems, the management system is able to store/access many payment sources and provide the payment source that is most beneficial to the user. The management system is also able to be implemented on other devices as well (e.g., personal computer).

Figure 6:
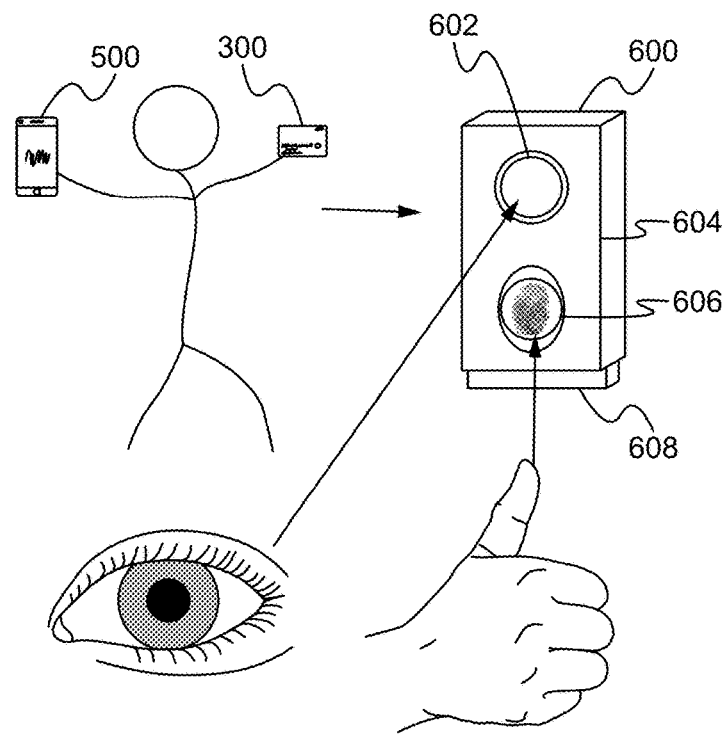
FIG. 6 illustrates a diagram of a pay station according to some embodiments.

FIG. 6 illustrates a diagram of a pay station according to some embodiments. The pay station 600 is able to include a retina scanner 602, a magnetic strip reader 604, a fingerprint 606 scanner, a chip reader 608 and/or any other device for payment receipt and/or security. The pay station 600 is able to include a processor, memory and programming to perform digital payments (e.g., Apple Pay) from a mobile device 500 and/or perform other functions. The pay station 600 is able to receive the universal card 300 using the magnetic strip reader 604, the chip reader 608 and/or the digital payment programming. The retina scanner 602 and/or the fingerprint scanner 608 are able to be used for user verification.

In some embodiments, the retina scanner 602 and/or the fingerprint scanner 608 are able to include a pulse detection mechanism to prevent fraud. Pulse detection or other determinations that a fake finger is not being used is able to include laser triangulation and utilizing light within the fingerprint detection device to measure internal bodily features of the finger such as blood movement. For example, the fingerprint scanner uses a laser to detect movement of internal structures (e.g., veins) by triggering a laser, then detecting reflections of the laser including an amount of time for the reflections to be received, measuring a delta in reflection time, and if there is a change (e.g., above a threshold), then the change is due to movement of internal structures such as due to blood flow, which indicates that the user is alive. A similar system is able to be included in the retina scanner.

In some embodiments, the management system is able to be used with the fingerprint scanner 608 and/or retina scanner 602 without the universal card 300. For example, a user places his finger in the fingerprint scanner 608 which is able to identify the user, and then based on the user identification, determine that the user has access to the management system which then automatically selects the appropriate payment source. Any other security measures are able to be utilized to prevent misuse and theft of a user's identity.

Figure 7:
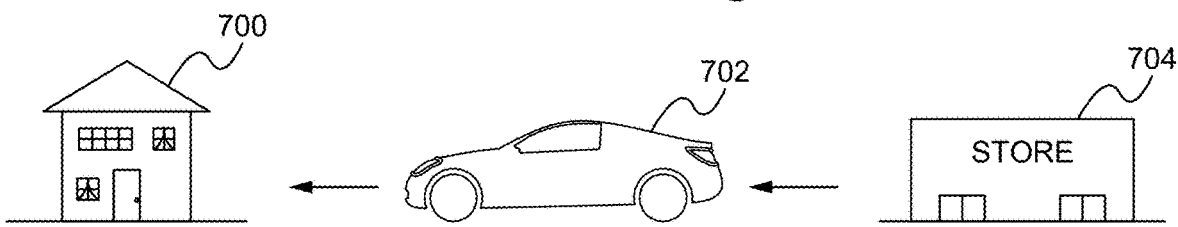
FIG. 7 illustrates a diagram of an autonomous delivery system implementing the management system according to some embodiments.

FIG. 7 illustrates a diagram of an autonomous delivery system implementing the management system according to some embodiments. Based on a user's purchase history which is able to be recorded and analyzed by the management system, the management system is able to utilize an autonomous delivery system for future purchases. Using an autonomous delivery system, items at a store 704 are able to be gathered and transported using a vehicle 702 to the user's house 700. The store 704 is able to be the store that the user has previously shopped at or a comparable store as determined by the management system and/or the user. In some embodiments, the management system does price comparisons of stores to help determine the best prices for comparable items. The store 704 is able to be an automated store where devices/systems are able to gather items for delivery. The store 704 is able to be a non-automated store where a human gathers the items for delivery. Once the items are gathered, the items are transported using a vehicle 702. The vehicle 702 is able to be any vehicle such as an autonomous car/truck, a drone (autonomous or not), a non-autonomous car/truck with a driver and others. The vehicle 702 is used to deliver the items at the user's house 700 or another destination.

In an example of a fully automated system, an autonomous store 704 utilizes machinery such as robots and conveyor belts to move items into a transport device (e.g., a box). The gathered items are then placed in or are retrieved by a vehicle 702 (e.g., autonomous drone) which is able to utilize mapping information and GPS to transport the items to the user's house 700. In some implementations, the vehicle 702 leaves the items at the user's doorstep or another location. In some implementations, the vehicle 702 (e.g., drone) is able to enter the house automatically (e.g., via a digital doorlock which is accessible by the automated vehicle, and place the items in the refrigerator and/or other locations inside the house. Upon completing the delivery, the vehicle 702 is able to leave the house, lock the digital lock, and return to the store 704 or another location.

Any aspects of a delivery system using the management system are able to be performed manually or autonomously.

Figure 8:
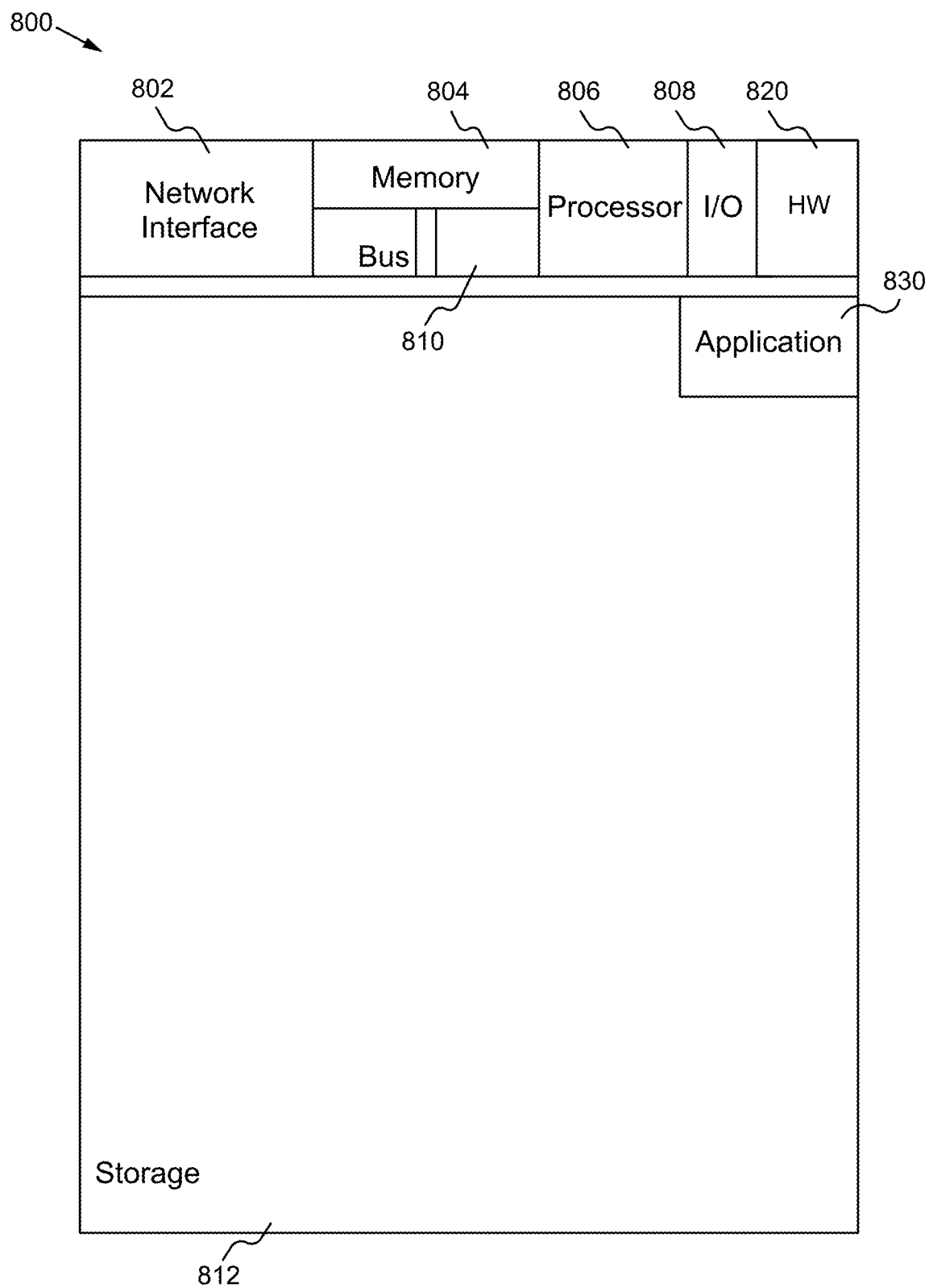
FIG. 8 illustrates a block diagram of an exemplary computing device configured to implement the management system according to some embodiments.

FIG. 8 illustrates a block diagram of an exemplary computing device configured to implement the management system according to some embodiments. The computing device 800 is able to be used to acquire, store, compute, process, communicate and/or display information. The computing device 800 is able to implement any of the management system aspects. In general, a hardware structure suitable for implementing the computing device 800 includes a network interface 802, a memory 804, a processor 806, I/O device(s) 808, a bus 810 and a storage device 812. The choice of processor is not critical as long as a suitable processor with sufficient speed is chosen. The memory 804 is able to be any conventional computer memory known in the art. The storage device 812 is able to include a hard drive, CDROM, CDRW, DVD, DVDRW, High Definition disc/drive, ultra-HD drive, flash memory card or any other storage device. The computing device 800 is able to include one or more network interfaces 802. An example of a network interface includes a network card connected to an Ethernet or other type of LAN. The I/O device(s) 808 are able to include one or more of the following: keyboard, mouse, monitor, screen, printer, modem, touchscreen, button interface and other devices. Management system application(s) 830 used to implement the management system method are likely to be stored in the storage device 812 and memory 804 and processed as applications are typically processed. More or fewer components shown in FIG. 8 are able to be included in the computing device 800. In some embodiments, management system hardware 820 is included. Although the computing device 800 in FIG. 8 includes applications 830 and hardware 820 for the management system, the management system is able to be implemented on a computing device in hardware, firmware, software or any combination thereof. For example, in some embodiments, the management system applications 830 are programmed in a memory and executed using a processor. In another example, in some embodiments, the management system hardware 820 is programmed hardware logic including gates specifically designed to implement the management system.

In some embodiments, the management system application(s) 830 include several applications and/or modules. In some embodiments, modules include one or more sub-modules as well. In some embodiments, fewer or additional modules are able to be included.

Examples of suitable computing devices include a personal computer, a laptop computer, a computer workstation, a server, a mainframe computer, a handheld computer, a personal digital assistant, a cellular/mobile telephone, a smart appliance, a gaming console, a digital camera, a digital camcorder, a camera phone, a smart phone, a portable music player, a tablet computer, a mobile device, a video player, a video disc writer/player (e.g., DVD writer/player, high definition disc writer/player, ultra high definition disc writer/player), a television, a home entertainment system, an augmented reality device, a virtual reality device, smart jewelry (e.g., smart watch), a vehicle (e.g., a self-driving vehicle), a universal card, a pay station, or any other suitable computing device.

The computing device is able to implement any of the health management aspects described herein.

An automated, dynamic digital health management tool is described herein. The health management tool records/documents every food item and/or other health-related products/services (e.g., treadmill/gym membership) purchased. The recordation/documentation of the purchases includes downloading/recording nutritional information, the SKU code, brand/product information, the company/store, where the item/service was purchased, and/or other information. The nutritional information is able to include any nutritional information such as calories, fat, sodium, protein, vitamins, minerals, and/or any other information. The documentation enables a company/manufacturer/store to provide marketing (e.g., coupons) and recall information to the user. The health management tool is able to be used to provide information for a user regarding what and when to eat. The health management tool provides guidance of where to purchase certain items such as gluten-free items, organic items, or any other item. Providing the guidance is able to be a monetization aspect.

A universal card is able to store information including financial information to purchase items, but also health/nutritional information.

Figure 9:
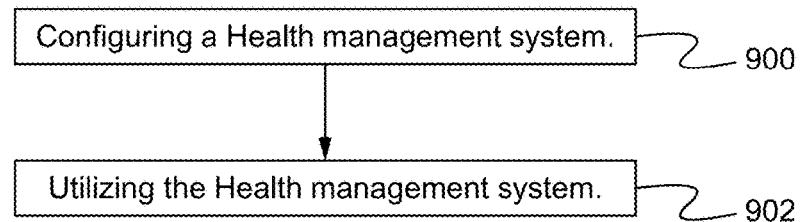
FIG. 9 illustrates a flowchart of a method of implementing a health management system according to some embodiments.

FIG. 9 illustrates a flowchart of a method of implementing a health management system according to some embodiments. In the step 900, the health management system is configured for a user. Configuring the health management system is able to be performed manually, automatically or semi-automatically. Configuring is able to include a user subscribing to the health management system. Subscribing is able to be performed similarly to other subscriptions such as inputting personal information and/or retrieving personal information (e.g., from a social networking site). After subscribing, the user's health and/or financial information is acquired. The user is able to manually input information such as height, weight, age, current medical conditions, allergies/sensitivities, desired/goal weight, fitness goals, and/or any other health information. The user is also able to manually input information such as credit card information, bank account information, and/or any other financial information. In a semi-automatic implementation, the user is able to manually enter some health and/or financial information, and the system (e.g., server) is able to acquire additional health and/or financial information of the user. In another example, the user provides his social security number, and the system retrieves medical and/or banking information associated with the user (e.g., from online health records from a doctor's office and/or banking records), but the user inputs other information not found by the automated search. In an automatic implementation, the system automatically retrieves the user's health and/or financial information. For example, based on facial recognition (or other biometric recognition), the system determines who the user is, and then accesses health and/or financial information for that user by communicating with hospital/doctor's offices, banks, credit card companies, and other medical/financial companies.

Configuring the health management system is able to include providing personal preferences and goals. For example, users are able to provide food preferences, grocery store preferences, exercise routines, weight goals, health goals, and/or any other preferences/goals. Users are also able to indicate which activities they enjoy and/or any equipment (e.g., exercise equipment, running apparel, smart watch/fitness band) which are able to be used with the health management system.

In the step 902, the health management system is utilized. Utilizing the health management system is able to include many different features such as acquiring nutritional information when a purchase is made. For example, the health management system acquires detailed information about a purchase including a SKU number or other identifying information, and the health management system is able to use that information to look up and download nutritional information. The health management system is also able to make suggestions to a user of what to purchase.

The health management system is able to make a suggestion at any time. For example, as the user is shopping, the health management system is able to indicate whether an item is a healthy pick or should be avoided based on the nutritional information (e.g., user scans an item's barcode to receive nutritional information). Determining whether the item is a healthy pick is able to be based on the nutritional facts, a user's health goal (e.g., lose 10 pounds), the user's medical history (e.g., food allergies/sensitivities) and/or any other factors. The suggestions are able to be based on financial management system information as well. For example, the suggestions are able to be based on a user's budget. Furthering the example, if the user has a budget of $100 per month for groceries, the health management system will suggest more inexpensive items compared to a user with a $1,000 budget. The suggestions are able to be based on more analysis such as determining which day of the month it is, analyzing shopping histories, factoring how much of the user's food budget is left, a determined or user-input preference of quantity versus quality, health/fitness goals, medical history and/or any other factors. For example, the user's current bank account is at $1,250, and if the user has indicated that he does not want his bank account to drop below $1,000, and there are no other expected expenses before the user's next paycheck at the beginning of the next month, the health management system is able to provide suggestions that keep the spending below $250. The suggestions are able to be each time an item is selected (e.g., scanned by a user's phone) or an entire purchase budget. For example, the health management system is able to provide a user a shopping list that factors in the user's budget, the user's health information, and the food nutritional information.

As the user is checking out at a grocery store, the health management system is able to indicate whether an item is acceptable for the user. For example, if the user is trying to lose weight, any items that have too many calories per serving are rejected for purchase. A warning is able to be provided to a user indicating that the item does not fit certain criteria or another action is able to be taken. In some embodiments, a smart pay station is able to access a user's health information and/or financial information to determine suggestions and/or allowable food items. In some embodiments, a user's mobile device and/or a server device are utilized to determine suggested and/or allowable food items.

As the user is shopping online, suggestions are able to be provided. The user's app or browser is able to highlight different items based on the user's health information and/or the items' nutritional information. For example, if the user is on a gluten-free diet, any items that contain gluten are grayed out, are not displayed, and/or another highlighting feature is implemented. Suggestions are able to be provided to the user (e.g., using pop-ups or a suggested page), where the suggestions are based on various health and/or financial information.

For autonomous shopping, the health management system is able to analyze the user's history of purchase and health information to automatically purchase or place items in a virtual shopping cart for purchase. For example, the health management system has received a doctor's diagnosis of diabetes, so items that have previously been purchased autonomously such as milk and vegetables are still able to be purchased, but based on the new health information, other previously purchased items such as cookies may be eliminated from the autonomous purchase. Additionally, to optimize savings and nutritional purchases, autonomous shopping is able to occur from multiple stores, where the health management system comparative shops among the stores within a specified area, and is able to make multiple purchases to be picked up or delivered to the user.

The health management system is able to provide a user with suggestions on when and what to eat. For example, if the user has a medical issue related to heartburn, doctors recommend avoiding eating within 3 hours of sleeping, so the health management system suggests the user eat at 6 pm to be finished with dinner before 7 pm, if the user's bed time is 10 µm. There are also dietary changes recommended for heartburn such as avoiding alcohol, spicy foods, acidic foods, and carbonated beverages, so when a user is shopping, the health management system suggests the user to buy water and mild foods and to avoid beer, soda and orange juice. In some embodiments, health management system displays a color-coded shopping list of food, where food items to avoid are grayed out, in red (or a red background) or are not even listed. In some embodiments, additional color-coding is used such as orange to indicate acceptable but not great options, and green to indicate the most appropriate options.

Similarly, to lose weight, the health management system is able to provide a detailed meal plan of what to eat and when to eat it. The meal plan is able to include total calories, fat, sugars, and any other information that may be helpful in a user achieving her goals. The meal plan is able to be part of a health plan which also includes details on when and how to exercise.

The health management system is also able to enable/perform targeted advertising based on the user's health information, purchases, financial information and/or other monitored information. As described, targeted advertising is able to include monitoring and analyzing the user's purchases, as well as monitoring and analyzing other financial information of the user. For example, the system monitors and tracks all of the individual items purchased by the user including any additional helpful information such as when purchased, how often purchased, purchased at which store, coupon used, are there any complementary items purchased/to be purchased (e.g., hamburger patties and buns), SKU number, expiration date, and/or any other information. The system is able to monitor the user's health information. The system is also able to monitor and analyze the user's income, other family member income, expenses, bank account information and other financial information which may be used to provide an advertisement that specifically targets the user. The targeted advertisement is able to be appropriately timed (e.g., when the previously purchased product is about to expire), based on the financial status of the user, based on the health status of the user, to provide a complement to a previously purchased item, based on a special event (e.g., birthday, anniversary, child's birth) and/or any other relevant information. The targeted advertising is able to be based on any characteristic of the user such as sex/gender, age, marital/relationship status, and/or any other characteristics. The targeted advertising is able to be presented to the user in any manner such as a mobile device (or any device) associated with the subscription (e.g., via corresponding login information or social networking information).

The health management system enables users to sell/buy products/services, including making suggestions of products/services to buy/sell. For example, if a user is trying to improve her stamina, the health management system is able to recommend exercise equipment such as a treadmill. Since the health management tool includes or is able to be used in conjunction with the financial management tool, the suggestion is able to be tailored specifically to the user based on the user's financial status. For example, a college student trying to get into better shape based on analyzed health information, receives a suggestion to purchase a low-end treadmill and/or some exercise weights, as opposed to a wealthy businessperson who receives a suggestion to purchase a high-end treadmill and/or a full set of home gym equipment. By taking into account a user's financial situation and/or other information such as living arrangements (e.g., dorm versus large house), as well as their health information, more accurate and helpful suggestions are able to be provided. In conjunction or as a follow up to the suggestion of fitness equipment, additional suggestions are able to be provided (e.g., running shoes). Again, the suggestion would be tailored based on specific user details and more generic information such as overall ratings and/or reviews from reviewers/consumers. By providing a mixed tailored suggestion, each user is able to receive the best option based on their budget and for their specific health situation.

In some embodiments, fewer or additional steps are implemented. In some embodiments, the order of the steps is modified.

Companies are able to utilize health information to provide guidance/suggestions of where to purchase items. For example, if a user is specifically looking for an allergen-free item (e.g., gluten-free, soy free, dairy free) or organic foods, companies are able to send information to the user. For example, online companies are able to provide an advertisement (e.g., within an app or on a web page), a communication (e.g., text message, email, Facebook posting), a coupon, and/or any other information to guide the user to their store and/or their products. The companies are able to provide tiered advertisements/information, so that the appropriate advertisement reaches the user. For example, a supermarket generates an advertisement for a lower priced organic food to be provided to those looking for organic foods but have less money in their bank accounts, and the supermarket generates a different advertisement for a higher priced organic food to be provided to those looking for organic foods and have bank accounts above a money threshold. In some embodiments, the companies do not have access to the financial management information and/or health management information, so the companies merely provide the different advertisements/information, and the health/financial management system provides the appropriate advertisement/information to the appropriate user based on their specific health/financial information/status. The health/financial management system is able to receive a payment from the companies for providing the targeted advertisements/information.

In some embodiments, the physical pay station described herein is able to acquire health information from the user in addition to or instead of the biometric scanning. For example, the pay station is configured to check oxygen levels, blood pressure and/or any other health information of the user. The health information is able to be stored and used by the health management system.

In some embodiments, the financial management system is configured to manage cash (e.g., dollar bills and coins or their equivalents). A user/business is able to take a picture of money (e.g., pictures of each side of a dollar bill). A physical pay station (and/or an enhanced scanner) is configured to scan/acquire images of money. Once the cash is scanned/photographed, the money is deposited into a user's bank account or another account (e.g., a business's account). The deposited cash is able to be accessed using the universal card (e.g., a user deposits the cash by taking a photograph and then uses his universal card which accesses the deposited cash to purchase items). The physical currency is no longer usable until it is re-authorized by a bank. In some embodiments, the user is required to physically provide the physical currency to a bank or other designated business within a specified amount of time (e.g., 7 days); otherwise, the deposit is rejected/withdrawn.

Figure 10:
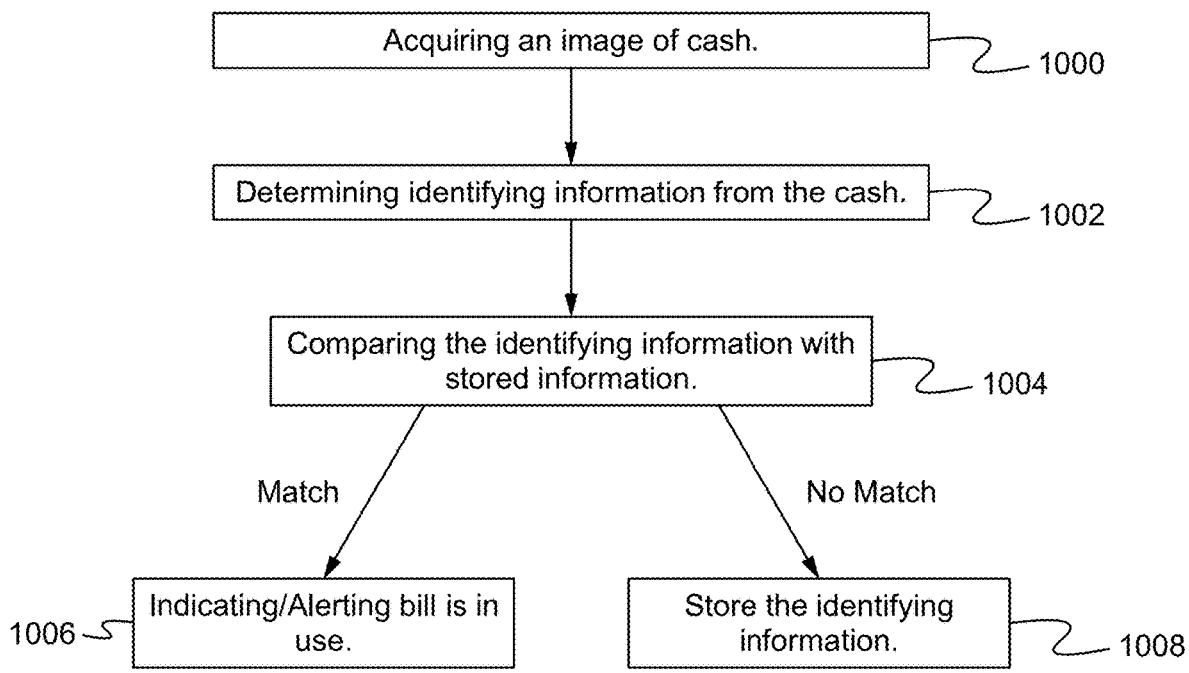
FIG. 10 illustrates a flowchart of a method of implementing a financial management system with physical currency according to some embodiments.

FIG. 10 illustrates a flowchart of a method of implementing a financial management system with physical currency according to some embodiments. In the step 1000, an image of physical currency (e.g., cash) is acquired. The image (or other capture) is acquired by taking a picture of both sides of the cash, scanning the cash to have a scan of the cash, or any other acquisition implementation.

In the step 1002, identifying information from the cash is determined. The identifying information is able to include a serial number or any other information which is unique to each individual bill. Determining the identifying information is able to be performed in any manner such as a mask and image-to-text scanning system. For example, since serial numbers are in the same location on a dollar bill (or any denomination), the remainder of the bill is able to be masked out, so that the image-to-text implementation is able to focus on just the serial number and not get confused with the imagery of the bill. The image-to-text implementation converts the masked image to a text version of the serial number. Any image-to-text implementation is able to be used (e.g., Optical Character Recognition (OCR)). A device (e.g., mobile device, scanner, server) is able to perform fraud detection by detecting a watermark and/or any other anti-counterfeiting measure. The identification information is able to be determined by any device such as a mobile device, a scanner device, or a server device. For example, an app on the mobile device or scanner device includes a feature to perform image processing to determine the serial number of the physical currency. In another example, the server device receives an image of the physical currency, and the server device includes software to process the image to determine the serial number.

In the step 1004, the text version of the serial number or other unique, identifying information is compared with a previously stored unique, identifying information. For example, a serial number of a current bill is compared with a database storing previously acquired serial numbers.

If a match is found, then an indication is made that the bill is not available for use, in the step 1006. For example, an alert is provided to a clerk/cashier receiving the bill that the bill has already been used (e.g., via a photograph/scan), and that the bill is currently worthless.

If a match is not found, then the identifying information is stored in a database or other data structure (e.g., a centralized database configured for storing acquired serial numbers), in the step 1008. The transaction is able to occur since the bill is a valid, unused bill. Either party in the transaction is able to store the used bill, and in some embodiments, the bill is able to be taken to the bank for re-authorization of the bill to be used again, where the serial number is removed from the database, and the bill is able to re-enter circulation.

In some embodiments, fewer or additional steps are implemented. In some embodiments, the order of the steps is modified.

Figure 11:
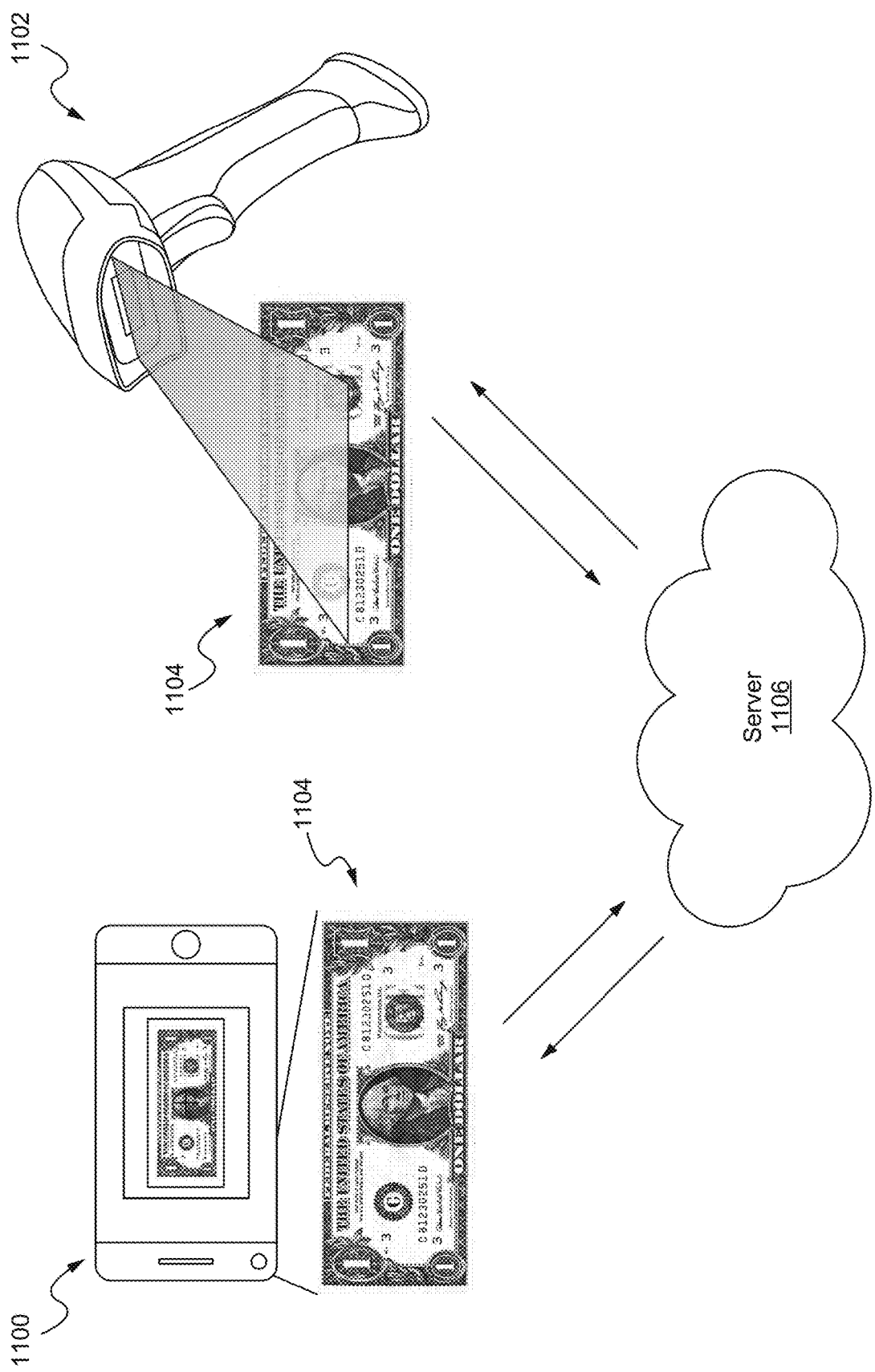
FIG. 11 illustrates a diagram of exemplary acquisition devices according to some embodiments.

FIG. 11 illustrates a diagram of exemplary acquisition devices according to some embodiments. A smart phone/camera 1100 is able to be used to take pictures of physical currency 1104 (e.g., $1, $2, $5, $10, $20, $50, $100 and other physical currency). For example, a user is able to use her smart phone 1100 to take a picture of one or both sides of a dollar bill. The images of the physical currency 1104 are able to be processed by the smart phone 1100, and the unique identification information is compared with unique identification information stored on a secure server device 1106. For example, the unique identification information is able to be sent to the server device 1106 which compares the unique identification information with the stored unique identification information, and if a match is not found, the new unique identification information is stored on the server device 1106. If a match is found, then an alert is sent by the server device 1106 to the smart phone 1100 and/or another device that the dollar bill has already been used. In some embodiments, the smart phone 1100 takes the picture of the physical currency 1104, and sends the picture to the server device 1106 which processes the picture to determine the identification information and performs the data comparison.

A scanner 1102 is able to be used to acquire unique identification information of the physical currency 1104. The scanner 1102 is able to take a picture to acquire the unique identification information. In some embodiments, another implementation is able to be used by the scanner 1102 to acquire the identification information such as a laser scanner. The images of the physical currency 1104 are able to be processed by the smart phone 1100, and the unique identification information is compared with unique identification information stored on a secure server device 1106. For example, the unique identification information is able to be sent to the server device 1106 which compares the unique identification information with the store unique identification information, and if a match is not found, the new unique identification information is stored on the server device 1106. If a match is found, then an alert is sent by the server device 1106 to the scanner 1102 and/or another device that the dollar bill has already been used.

To utilize the management system, a user inputs financial information such as credit card numbers and bank account information, and/or financial information is able to be retrieved automatically. The management system is able to be implemented with user assistance or automatically without user involvement.

In operation, the management system enables a user to manage the user's finances in a variety of ways including paying for goods and services using a desired line of credit or other account. The management system is also able to be used to provide targeted advertising based on the user's purchases. An autonomous system is able to utilize the management system to provide users with goods and services at appropriate times. The health management system is able to be utilized separately, in conjunction with the financial management system or be incorporated with the financial management system.

The present invention has been described in terms of specific embodiments incorporating details to facilitate the understanding of principles of construction and operation of the invention. Such reference herein to specific embodiments and details thereof is not intended to limit the scope of the claims appended hereto. It will be readily apparent to one skilled in the art that other various modifications may be made in the embodiment chosen for illustration without departing from the spirit and scope of the invention as defined by the claims.

What is claimed is:

1. A method comprising:
acquiring, with a device, an image of physical currency;
determining identifying information from the image of the physical currency;
receiving a result based on a comparison of the identifying information with stored identifying information;
taking an action based on the result of the comparison of the identifying information with the stored identifying information, wherein taking the action includes depositing an amount of money equivalent to the physical currency into a bank account of a user; and
enabling use of the deposited money with a universal card;
scanning the universal card with a scanning device, the scanning device configured for: performing at least one of a fingerprint scan with life verification or a retina scan with life verification, wherein the life verification includes using a laser to detect movement of internal structures, detecting reflections of the laser including timing of receiving the reflections, measuring a delta in the reflection times, and if the delta is detected, then it is determined the user is alive.

2. The method of claim 1 wherein acquiring the image of the physical currency comprises taking a picture of one or both sides of the physical currency.

3. The method of claim 1 wherein determining the identifying information from the image of the physical currency comprises implementing image processing including a mask and image-to-text conversion to retrieve a serial number in text.

4. The method of claim 1 wherein taking the action includes blocking a transaction and indicating that the physical currency is unavailable for use.

5. The method of claim 4 wherein indicating that the physical currency is unavailable for use includes providing an alert on the device.

6. The method of claim 1 wherein taking the action includes storing the identifying information with the stored identifying information.

7. The method of claim 1 wherein taking the action includes allowing a transaction.

8. An apparatus comprising:
a non-transitory memory for storing an application, the application for:
receiving an image of physical currency;
determining identifying information from the image of the physical currency;
sending a result based on a comparison of the identifying information with stored identifying information;
taking an action based on the result of the comparison of the identifying information with the stored identifying information, wherein taking the action includes depositing an amount of money equivalent to the physical currency into a bank account of a user; and
enabling use of the deposited money with a universal card, wherein the universal card is configured to be scanned by a scanning device configured for: performing at least one of a fingerprint scan with life verification or a retina scan with life verification, wherein the life verification includes using a laser to detect movement of internal structures, detecting reflections of the laser including timing of receiving the reflections, measuring a delta in the reflection times, and if the delta is detected, then it is determined the user is alive; and
a processor coupled to the memory, the processor configured for processing the application.

9. The apparatus of claim 8 wherein receiving the image of the physical currency comprises receiving a picture of one or both sides of the physical currency.

10. The apparatus of claim 8 wherein determining the identifying information from the image of the physical currency comprises implementing image processing including a mask and image-to-text conversion to retrieve a serial number in text.

11. The apparatus of claim 8 wherein taking the action includes blocking a transaction and indicating that the physical currency is unavailable for use.

12. The apparatus of claim 11 wherein indicating that the physical currency is unavailable for use includes sending an alert to a mobile device.

13. The apparatus of claim 8 wherein taking the action includes storing the identifying information with the stored identifying information.

14. The apparatus of claim 8 wherein taking the action includes allowing a transaction.

15. A system comprising:
a scanner device configured for:
acquiring an image of physical currency; and
determining identifying information from the image of the physical currency; and
a server device configured for:
determining a result based on a comparison of the identifying information with stored identifying information;
taking an action based on the result of the comparison of the identifying information with the stored identifying information, wherein taking the action includes depositing an amount of money equivalent to the physical currency into a bank account of a user; and
enabling use of the deposited money with a universal card
a scanning device configured for: performing at least one of a fingerprint scan with life verification or a retina scan with life verification, wherein the life verification includes using a laser to detect movement of internal structures, detecting reflections of the laser including timing of receiving the reflections, measuring a delta in the reflection times, and if the delta is detected, then it is determined the user is alive, wherein the universal card is configured to be scanned by the scanning device.

16. The system of claim 15 wherein acquiring the image of the physical currency comprises taking a picture of one or both sides of the physical currency.

17. The system of claim 15 wherein determining the identifying information from the physical currency comprises implementing image processing including a mask and image-to-text conversion to retrieve a serial number in text.

18. The system of claim 15 wherein taking the action includes blocking a transaction and indicating that the physical currency is unavailable for use.

19. The system of claim 18 wherein indicating that the physical currency is unavailable for use includes sending an alert to the scanner device.

20. The system of claim 15 wherein taking the action includes storing the identifying information with the stored identifying information.

21. The system of claim 15 wherein taking the action includes allowing a transaction.

* * * * *